United States Patent [19]

Wätjen et al.

[11] Patent Number: 4,622,321
[45] Date of Patent: Nov. 11, 1986

[54] OXADIAZOLYLIMIDAZOBENZODIAZEPINE, COMPOSITIONS, AND METHOD

[75] Inventors: Frank Wätjen, Bagsvaerd; Mogens Engelstoft, Vaerløse; John B. Hansen, Lyngby; Leif H. Jensen, Hellerup, all of Denmark

[73] Assignee: AS Ferrosan, Søborg, Denmark

[21] Appl. No.: 816,731

[22] Filed: Jan. 6, 1986

[30] Foreign Application Priority Data

May 17, 1985 [DK] Denmark ............................. 2204/85
Aug. 12, 1985 [DK] Denmark ............................. 3659/85
Oct. 17, 1985 [DK] Denmark ............................. 4769/85

[51] Int. Cl.[4] ..................... A61K 31/55; C07D 487/04
[52] U.S. Cl. ................................... 514/220; 548/131; 540/498
[58] Field of Search .................. 260/239.3 T; 514/220

[56] References Cited

U.S. PATENT DOCUMENTS

| | | | |
|---|---|---|---|
| 4,031,029 | 6/1977 | Mohrbacher et al. | 260/239.3 B |
| 4,316,839 | 2/1982 | Gerecke et al. | 260/239.3 T |
| 4,359,420 | 11/1982 | Gerecke et al. | 260/239.3 T |
| 4,435,403 | 3/1984 | Braestrup et al. | 546/86 |
| 4,507,313 | 3/1985 | Braestrup et al. | 260/239.3 T |

FOREIGN PATENT DOCUMENTS

| | | | |
|---|---|---|---|
| 245/85 | 1/1985 | Denmark | 260/239.3 T |
| 27214 | 4/1981 | European Pat. Off. | 260/239.3 T |
| 54507 | 6/1982 | European Pat. Off. | 546/86 |
| 109921 | 3/1984 | European Pat. Off. | 260/239.3 T |
| 150040 | 7/1985 | European Pat. Off. | 260/239.3 T |
| 225/84 | 1/1984 | Switzerland | 260/239.3 T |
| 3149/84 | 6/1984 | Switzerland | 260/239.3 T |
| 5123/84 | 10/1984 | Switzerland | 260/239.3 T |

OTHER PUBLICATIONS

Squires, Braestrup, "Benzodiazepine Receptors in Rat Brain", Nature 266, (1977) pp. 732–734.
Litchfield et al., "A Simplified Method of Evaluating Dose-Effect Experiments", Journal of Pharmacology and Experimental Therapeutics (1949) pp. 99–113.
Hartman et al., "A Novel 1,3-Thiazole Synthesis Via Alpha-Metallated Isocyanides and Thiono Esters", Synthesis (1976) pp. 681–682.
Chang et al., "Benzodiazepine Receptors: Labeling in Intact Animals with [$^3$H] Flunitrazepam", Europe. J. Pharmacol. 48 (1978) pp. 213–218.

Primary Examiner—Robert T. Bond
Attorney, Agent, or Firm—Gordon W. Hueschen

[57] ABSTRACT

The application discloses a novel benzodiazepine agonist compound, namely, 3-(5-cyclopropyl-1,2,4-oxadiazol-3-yl)-5,6-dihydro-5-methyl-6-oxo-4H-imidazo [1,5-a][1,4]benzodiazepine, pharmaceutical compositions thereof, and a method of ameliorating central nervous system ailments therewith, especially convulsions and anxiolytic states. A novel intermediate and process for its production are also disclosed.

4 Claims, No Drawings

OXADIAZOLYLIMIDAZOBENZODIAZEPINE, COMPOSITIONS, AND METHOD

BACKGROUND OF INVENTION

1. Field of Invention

This invention relates to a novel oxadiazolyl imidazobenzodiazepine compound, pharmaceutical compositions thereof, method of treating therewith, and to methods of preparing such compound. The novel compound is useful in psychopharmaceutical applications, e.g., in the treatment of central nervous system ailments, for example, as an anti-convulsant or an anxiolytic.

2. Prior Art

It is well known (Squires, R. F. and Braestrup, C., Nature (London) 266, (1977) 734) that specific sites in the central nervous systems of vertebrates exhibit a high specific affinity for binding 1,4- and 1,5-benzodiazepines. These sites are called benzodiazepine receptors.

Ferrosan European patent application No. 109,921 (published May 30, 1984) and corresponding U.S. Pat. No. 4,507,313 (filed Nov. 15, 1983, issued Mar. 26, 1985) disclose compounds having the general Formula I

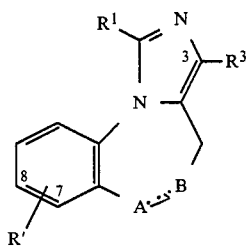

wherein
R' is hydrogen, chlorine, fluorine, or nitro in the 7- or 8-position
$R^1$ is hydrogen or lower-alkyl of up to 3 carbon atoms,
$R^3$ is an oxadiazolyl of the formula

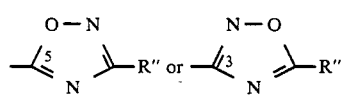

wherein
R" is lower-alkyl of up to 3 carbon atoms,
A···B is a grouping of the formula

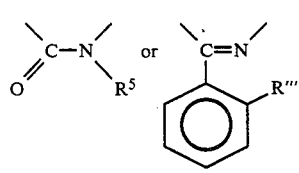

wherein
$R^5$ is hydrogen or methyl, and
R''' is hydrogen or chlorine.

This U.S. Pat. No. 4,507,313 further discloses (Column 1, lines 59 through Column 2, line 4) that such oxadiazolyl benzodiazepines of EP No. 27,214 (U.S. Pat. No. 4,316,839) column 4, line 2 and oxadiazolyl beta-carbolines, as disclosed in earlier European patent application No. 54,507 (U.S. Pat. No. 4,435,403), exhibit stronger binding affinity for the benzodiazepine receptors than the analogous substituted compounds which are alkyl esters (rather than such oxadiazolyl derivatives). Roche European patent application No. 150,040 (published July 31, 1985) and corresponding Danish patent application No. 245/85 (made available July 22, 1984) and the presumed corresponding U.S. patent application also disclose oxadiazolyl imidazobenzodiazepines.

The disclosure of Roche European patent application No. 150,040 is very broad. Its disclosure of 1,2,4-oxadiazolyl-benzodiazepine compounds can be illustrated by Formulas II and III.

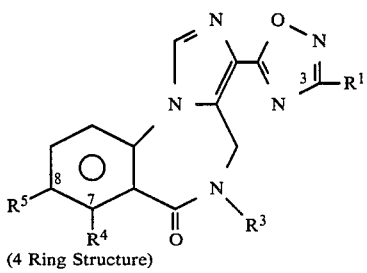

(4 Ring Structure)

wherein
$R^1$ = alkyl, cycloalkyl, methoxymethyl
$R^3$ = H, $CH_3$, and
$R^4$, $R^5$ = H, halogen

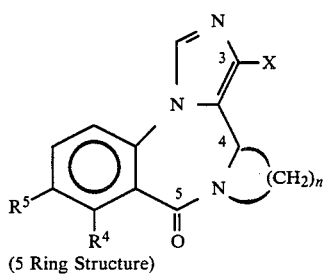

(5 Ring Structure)

wherein
X =

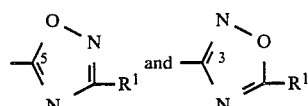

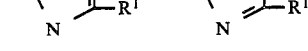

wherein
$R^1$ = alkyl, cycloalkyl, $CF_3$, or methoxymethyl
$R^4$, $R^5$ = H, halogen, $CF_3$, and
n = 2 or 3.

The compounds of Roche EP No. 150,040 examples 2, 3, 16, and 43 are old compounds of Ferrosan U.S. Pat. No. 4,507,313 column 2, lines 5-6, and examples 2 and 3 are preferred compounds of Roche EP No. 150,040 page 5 lines 34-37.

The compounds of Roche EP No. 150,040 examples 2, 3, 16, 29, 32, 43, 44, 45, 49, 50, 51, 52, 53, and 56 are 5,6-dihydro-6-oxo-4H-imidazo[1,5-a][1,4]benzodiazepine compounds.

The compounds of Roche EP No. 150,040 examples 1, 8, 9, 17, 18, 23, 30 are 10,11,12,12a-tetrahydro-9-oxo-9H-imidazo-[1,5-a]azeto[2,1-c][1,4]benzodiazepine compounds.

The compounds of Roche EP No. 150,040 examples 4, 5, 6, 7, 10, 11, 12, 13, 14, 15, 19, 20, 21, 22, 24, 25, 26, 27, 28, 31, 33, 34, 35, 36, 37, 38, 39, 40, 41, 42, 46, 48, 54, 55, 57, 58 and 59 are 11,12,13,13a-tetrahydro-9-oxo-9H-imidazo-[1,5-a]pyrrolo[2,1-c][1,4]benzodiazepine compounds.

The compound of Roche EP No. 150,040 example 47 is an 11,13a-dihydro-9-oxo-9H-imidazo[1,5-a]pyrrolo[2,1-c][1,4]benzodiazepine compound.

The compounds of Roche EP No. 150,040 examples 11, 15, 26, and 40 are 1,2,4-oxadiazol-3-yl compounds.

The compounds of Roche EP No. 150,040 examples 11, 15, 26, and 40 are 1,2,4-oxadiazol-3-yl compounds. combined with an 11,12,13,13a-tetrahydro-9-oxo-9H-imidazo[1,5-a]pyrrolo[2,1-c][1,4]benzodiazepine skeleton.

The compound of Roche EP No. 150,040 Example 40 is a 5-cyclopropyl-1,2,4-oxadiazol-3-yl compound with an 11,12,13,13a-tetrahydro-9-oxo-9H-imidazo[1,5-a]pyrrolo[2,1-c][1,4]benzodiazepine skeleton.

The compound of Roche EP No. 150,040 Example 40 is a 5-cyclopropyl-1,2,4-oxadiazol-3-yl compound which has been found grossly inferior in pharmacological and biochemical evaluations as further reported hereinafter.

Of specific interest to the present invention, the Roche patent application EP No. 150,040 discloses the following compounds

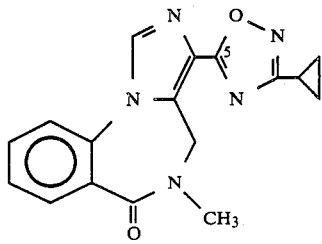

EXAMPLE 44
a 3-cyclopropyl-1,2,4-oxadiazol-5-yl compound and

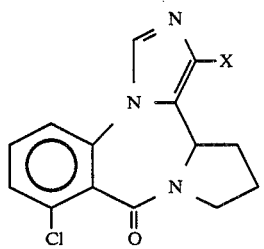

wherein

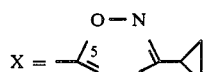

EXAMPLE 31
a 3-cyclopropyl-1,2,4-oxadiazol-5-yl compound

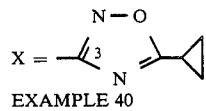

EXAMPLE 40
a 5-cyclopropyl-1,2,4-oxadiazol-3-yl compound

Roche European patent application No. 150,040 further claims a process for the preparation of such compounds (II and III) by reacting compounds of Formula IV and V

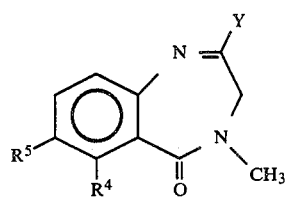

IV

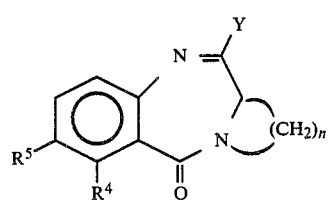

V wherein $R^4$, $R^5$ and n have the meanings set forth in the foregoing and Y is a leaving group, with a compound of the formula $$CN-CH_2-X$$

wherein X has the meaning set forth in the foregoing for Formula III.

All oxadiazoles in the Roche application are actually made by reacting intermediates IV or V with CN—CH$_2$—CO$_2$R to form a compound of Formula IV or V having the additional substituent in place of Y wherein X is CO$_2$R, which is thereafter, in several steps, converted to an oxadiazole.

The new compound provided by the present invention has the same type of structure and activity as disclosed in the prior art, but the particular and specific compound of the present invention, and the particular and specific "subject matter as a whole", including not only its chemical structure but also its pharmacological properties, has been found to be both advantageous and unobvious from the standpoint of one skilled in the art.

OBJECTS

It is an object of the present invention to provide the novel compound 3-(5-cyclopropyl-1,2,4-oxadiazol-3-yl)-5,6-dihydro-5-methyl-6-oxo-4H-imidazo[1,5-a][1,4]benzodiazepine and pharmaceutically-acceptable acid addition salts thereof, which are useful in the treatment of central nervous system disorders or ailments, especially as anticonvulsants and anxiolytics, a process for producing the same, pharmaceutical compositions thereof, an intermediate therefor, and a method of treating therewith. Additional objects will become apparent hereinafter, and still others will be obvious to one skilled in the art.

SUMMARY OF THE INVENTION

The invention, in summary, comprises the following: A compound selected from the group consisting of 3-(5-cyclopropyl-1,2,4-oxadiazol-3-yl)-5,6-dihydro-5-methyl-6-oxo-4H-imidazo[1,5-a][1,4]benzodiazepine and a pharmaceutically-acceptable acid addition salt thereof; a pharmaceutical composition suitable for use in the treatment of central nervous system ailments, especially convulsions and anxiety states, comprising an effective amount of 3-(5-cyclopropyl-1,2,4-oxadiazol-3-yl)-5,6-dihydro-5-methyl-6-oxo-4H-imidazo[1,5-a][1,4]benzodiazepine or a pharmaceutically-acceptable acid addition salt thereof, a method of treating such ailments or disorders in a subject in need thereof comprising the step of administering to the subject an amount of 3-(5-cyclopropyl-1,2,4-oxadiazol-3-yl)-5,6-dihydro-5-methyl-6-oxo-4H-imidazo[1,5-a][1,4]benzodiazepine or a pharmaceutically-acceptable acid addition salt thereof effective for such purpose; andd such a method wherein the active compound is administered in the form of a pharmaceutical composition containing also a pharmaceutically-acceptable carrier or diluent. The invention also comprises a method of synthesizing the compound of the invention, and a new intermediate therefor.

The free basic compound of the present invention has the formula

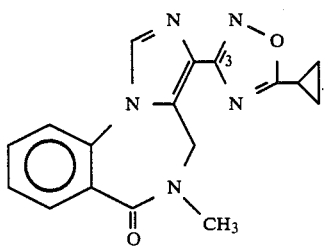

M.p. 179°–180.8° C.

This compound can be prepared either by conventional methods analogous to the methods described in Ferrosan U.S. Pat. No. 4,507,313 Example 3, Roche EP No. 150,040 Example 40, or Schering U.S. Pat. No. 4,435,403 Example 70 as illustrated below

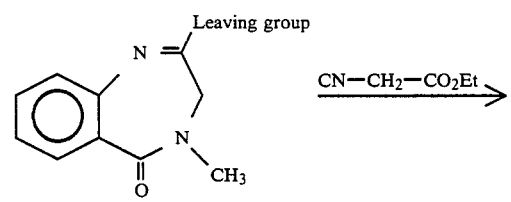

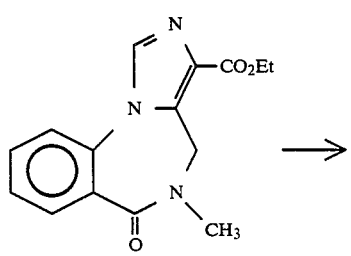

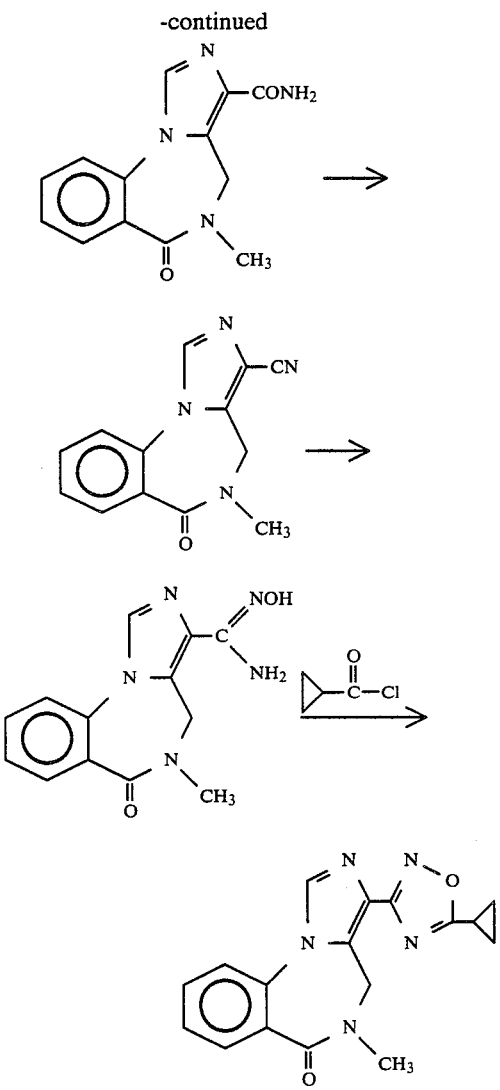

or by the new method provided by the present invention and as illustrated below

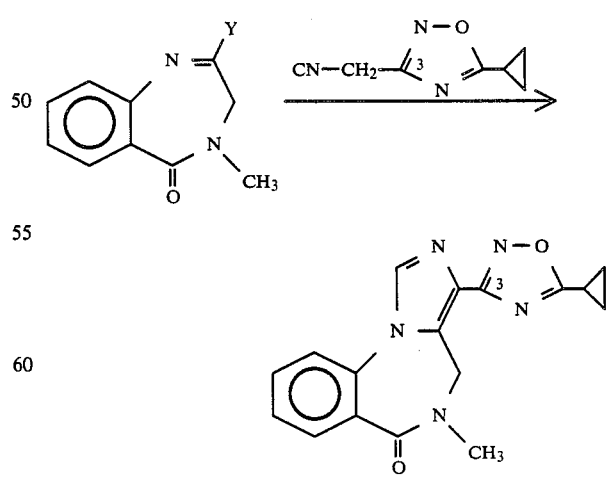

wherein
Y is a leaving group, such as the —OP(O)(O-ethyl)$_2$ group of Example 6 hereof. Alternatively, the leaving group may be any disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)$_2$ wherein R is lower-alkyl or —OP(O)(NR'R") wherein R' and R" each represents lower-alkyl, allyl, or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is non-reactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty ($-40$) degrees Celsius to about room temperature is accordingly usually particularly suitable.

PHARMACEUTICAL COMPOSITIONS

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating (or benzodiazepine agonistic) amount of the active ingredient commensurate with the intended daily dosage range to be employed. Tablets containing ten (10) milligrams of active ingredient or, more broadly, ten (10) to thirty (30) milligrams, per tablet, are accordingly suitable representative unit dosage forms. The compound of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are conveniently unit dosages.

For oral application, particularly suitable are tablets, dragees, or capsules having talc and/or a carbohydrate carrier or binder or the like, the carrier preferably being lactose and/or corn starch and/or potato starch. A syrup, elixir or the like can be used when a sweetened vehicle can be employed. Generally, as to broader ranges, the compound of the invention is dispensed in unit dosage form comprising 0.05–100 mg in a pharmaceutically-acceptable carrier per unit dosage.

METHOD OF TREATING

Due to its high degree of affinity for the benzodiazepine receptors, the compound of the invention is extremely useful in the treatment of central nervous system ailments or disorders, when administered in an amount effective for the alleviation, amelioration, or elimination thereof, which is of course also a benzodiazepine agonistic amount. The important CNS activity of the compound of the invention includes both anticonvulsant and anxiolytic activities along with a low toxicity, together presenting a most favorable therapeutic index. The compound of the invention may accordingly be administered to a subject, e.g., a living animal body, including a human, in need of the same for the treatment, alleviation, amelioration, or elimination of an indication, associated with the central nervous system and the so-called benzodiazepine receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to its benzodiazepine agonistic effect. Suitable dosage ranges are 1–200 milligrams daily, preferably 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge. Broader ranges for dosages of the compound according to this invention are 0.1–300 mg/day, preferably 1–30 mg/day, when administered to patients, e.g., humans, as a drug.

DETAILED DESCRIPTION OF THE INVENTION

The following Examples are given by way of illustration only, but are not to be construed as limiting.

EXAMPLE 1

5,6-dihydro-5-methyl-6-oxo-4H-imidazo[1,5-a][1,4]benzodiazepine-3-carboxamide oxime A mixture of 0.0125 mole 3-cyano-5,6-dihydro-5-methyl-6-oxo-4H-imidazo[1,5-a][1,4]benzodiazepine (prepared as in U.S. Pat. No. 4,316,839), 1.1 g of hydroxylamine hydrochloride, 200 ml of 99% ethanol and 5.2 ml of 20% potassium carbonate solution in water was heated with stirring for two hours. The reaction mixture was filtered and the filtrate was concentrated. The residue was treated with 100 ml of water and the crystalline solid was filtered off and washed with water.

M.p. 224.6°–225.9° C.

EXAMPLE 2

3-(5-cyclopropyl-1,2,4-oxadiazol-3-yl)-5,6-dihydro-5-methyl-6-oxo-4H-imidazo[1,5-a][1,4]benzodiazepine A mixture of 580 mg 5,6-dihydro-5-methyl-6-oxo-4H-imidazo[1,5-a][1,4]benzodiazepine-3-carboxamidoxime, 3 ml ethyl cyclopropylcarboxylate, 50 mg sodium and 3 g mol. sieves (4 Å) was refluxed for six hours in 50 ml dry ethanol. The reaction mixture was cooled, filtered and the filtrate was evaporated to give a residue as oily crystals. Treatment of the residue with water gave the title compound as white crystals.

M.p. 179°–180.8° C.

EXAMPLE 3

Formylaminomethyl-carboxamideoxime

To 53.6 g/0.638 mol/N-formylamino-acetonitrile* was added 0.55 mol freshly liberated hydroxylamine dissolved in 370 ml methanol. An ice bath was used to keep the temperature below 20° C. during the addition. The solution was allowed to stand at room temperature overnight, whereafter it was evaporated to give the title compound as pale crystals.
*Synthesis, Vol. 10, pp. 681–682

Decomp. 104°–110° C.

EXAMPLE 4

3-Formylaminomethyl-5-cyclopropyl-1,2,4-oxadiazole

A mixture of 35 ml ethylcyclopropyl carboxylate, 30 g formylaminomethyl-carboxamideoxime, 1 g sodium and 30 g crushed mol sieves (4 Å) was refluxed in 300 ml abs. EtOH for 8 hours whereafter a further 1 g sodium was added. The reaction mixture was filtered and the filtrate was evaporated. The dark oily residue was suspended in 300 ml $CHCl_3$, filtered and the filtrate was evaporated to give the title compound as an oil.

H-NMR (60 MHz, $CDCl_3$) σ (ppm): 1.2 (4H, m), 2.8 (1H, m), 4.5 (2H, d, j=6 Hz), 7.8 (1H, broad-NH), 8.2 (1H, s).

EXAMPLE 5

5-Cyclopropyl-3-isocyanomethyl-1,2,4-oxadiazole

A stirred solution of 5-cyclopropyl-3-formylaminomethyl-1,2,4-oxadiazole (60 mmol) and triethylamine (176 mmol) in $CH_2Cl_2$ (100 ml) was charged dropwise with $POCl_3$ (60 mmol) at 0° C., whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted and the solution was evaporated to give the title compound as an oil.

The oil was processed without any further purification. IR: $cm^{-1}$: 2160.

EXAMPLE 6

3-(5-cyclopropyl-1,2,4-oxadiazol-3-yl)-5,6-dihydro-5-methyl-6-oxo-4H-imidazo[1,5-a][1,4]benzodiazepine 3,4-dihydro-4-methyl-2H-1,4-benzodiazepine-2,5(1H)dione* (16.5 mmol) was dissolved in dry DMF (25 ml) and charged with K-t-butylate (18 mmol). The resulting solution was cooled under $N_2$ to −20° C., whereafter chlordiethylphosphate (20 mmol) was added.
*U.S. Pat. No. 4,316,839

The reaction mixture was kept under $N_2$ with stirring at −20° C. and charged with a −30° C. cold solution of 5-cyclopropyl-3-isocyanomethyl-1,2,4 oxadiazole (20 mmol) and K-t-butylate (20 mmol) in dry DMF (20 ml).

The resulting reaction mixture was allowed to heat to room temperature, whereafter it was evaporated to dryness in vacuo. The oily residue containing the crude product was purified on $SiO_2$ with ethyl acetate as eluent. This gave the title compound as white crystals.

M.p. 179°–180° C.

EXAMPLE 7

Representative Pharmaceutical Compositions (a) A typical tablet for use in treating anxiety states and which may be prepared by conventional tableting techniques contains

| | |
|---|---|
| Compound of Invention* | 1.0 mg |
| Lactosum (lactose) | 67.4 mg Ph. Eur. |
| Avicel ® (microcellulose) | 31.4 mg |
| Amberlite ® (IRP 88)** | .01 mg |
| Magnesii stearas (magnesium stearate) | 0.25 mg Ph. Eur. |

*possibly salt form
**ion exchange resin

Exactly the same tablet may be used for treating convulsions.

(b) For suppositories, any usual suppository base may be employed for incorporation thereinto by usual procedure of the active ingredient, such as a polyethyleneglycol which is a solid at normal room temperature but which melts at or about body temperature.

(c) For parenteral (including subcutaneous) sterile solutions, the active ingredient together with conventional ingredients in usual amounts are employed, such as sodium chloride, sodium dihydrogen phosphate, disodium edetate(ethylenediaminetetraacetic acid disodium salt), benzyl alcohol, sodium hydroxide to adjust pH, and double-distilled water q.s., according to conventional procedure, such as filtration, aseptic filling into ampoules, and autoclaving for sterility.

Other suitable pharmaceutical compositions will be immediately apparent to one skilled in the art.

PHARMACOLOGY

The compounds of the invention have been found to exhibit an unpredictably favourable and highly advantageous degree of activity in the standard classical test for determining the in vivo affinity for the benzodiazepine receptors, as well as in the standard test considered predictive for pharmaceutical activity against convulsions and anxiety states mediated through the benzodiazepine receptors.

The following test has been performed on the compound of the invention as well as on representative examples of prior art compounds.

I. In vivo inhibition of $^3$H-flunitrazepam binding to mouse forebrain membranes by test substances administered intraperitoneally. (Procedure 130)

Principle.

Twenty minutes after a dose of $^3$H-flunitrazepam ($^3$H-FNM) (200 μCi/kg, i.v.) the amount of specific $^3$H-FNM binding to brain benzodiazepine receptors has reached its maximal value. This specific binding of $^3$H-FNM can be partly or completely prevented by simultaneous or prior administration of pharmacologically active benzodiazepines and by some benzodiazepine-like agents (Chang and Snyder, Eur.J.Pharmacol. 48, 212-218 (1978)).

Test Procedure.

Suspensions of test substances (2 mg/ml) are prepared in 5% Duphasol-X* by sonification for 10 min using a Branson B15 microtip ultrasonifier (setting 7). Groups of three mice (female, NMR, 18-22 gram) are injected with the test substance at 100 mg/kg intraperitoneally. Fifteen minutes after test substance administration the mice are challenged with 4 μCi intraveneously of $^3$H-FNM (70-90 Ci/mole) in 200 μl physiological saline. Twenty minutes after $^3$H-FNM administration mice are sacrificed by decapitation, the forebrains rapidly excised (within 30 sec) and homogenized in 12 ml of icecold 25 mM $KH_2PO_4$, pH 7.1, using an Ultra-Turrax homogenizer fitted with an N 10 shaft. Two aliquots of 1 ml are immediately filtered through Whatman GF/C glassfibre filters and washed with 2×5 ml of the above mentioned buffer. The amounts of radioactivity on the filters are determined by conventional scintillation counting. One group of untreated mice serves as controls. One to three mice are injected with 25 mg/kg clonazepam i.p. 30 minutes before $^3$H-FNM to determine the amount of non-specific $^3$H-FNM binding, which should be between 8-15% of total binding.

*(TM Duphar; castor-oil-ethylene oxide derivative for emulsifying and solubilizing oil and other water-insoluble substances)

When doses of 100 mg/kg inhibit more than 50% of specific $^3$H-flunitrazepam binding; test substances are administered in doses, which are factors of 3.16 times lower than 100 mg/kg.

The $ED_{50}$ for a test substance is defined as that dose which inhibits 50% of specific $^3$H-FNM binding. Specific binding is the amount of binding in controls minus the amount binding in clonazepam-treated mice.

Results.

The $ED_{50}$ value is determined from dose response curves. If only one dose of test substance is administered the $ED_{50}$ value is calculated as follows, provided that the inhibition of specific binding is within the range of 25-75%:

$$ED_{50} = \text{(administered dose)} \times \frac{1 \times 1000}{\left(\frac{C_o}{C_x} - 1\right)} \mu g/kg$$

where $C_o$ is specific binding in controls and $C_x$ is specific binding in mice treated with test substance.

II. Pentazol clonic conv. mice (i.p.) (Procedure 400)

Principle.

Pentylenetetrazol induces clonic and tonic convulsions in mice at doses of 60-120 mg/kg s.c. The mechanism is unknown but seems to be due to some effects through the GABA receptor/benzodiazepine receptor/chloride ionophore complex. Antagonism of convulsions induced by maximal doses of pentylenetetrazol is considered predictive for drugs effective against petit mal epilepsia and anxiety.

Method.

150 mg/kg pentylenetetrazol dissolved in 0.9% NaCl is given by the subcutaneous route in volumes of 15 ml/kg to male or female NMRI mice weighing 20-25 g 30 min after an intraperitoneal injection of a test compound. Number of mice exhibiting clonic seizures is noted within the next 30 min. At least 3 doses of each test compound are used with 4 or 8 mice per dose, and with doses both above and below the $ED_{50}$ value.

Results.

The $ED_{50}$ value is calculated as the dose in μg/kg at which seizures are inhibited in 50% of the animals using a computer program based on the method of Litchfield and Wilcoxon (1949).

III. Pentazol tonic conv. mice i.p. (Procedure 401)

Principle.

Pentylenetetrazol induces clonic and tonic convulsions in mice at doses of 60-120 mg/kg s.c. The mechanism is unknown but seem to be due to some effects through the GABA receptor/benzodiazepine receptor/chloride ionophore complex. Antagonism of convulsions induced by maximal doses of pentylenetetrazol is considered predictive for drugs effective against petit mal epilepsia and anxiety.

Method.

150 mg/kg pentylenetetrazol (Pentazol, Sigma) dissolved in 0.9% NaCl is given by the subcutaneous route in volumes of 15 ml/kg to male or female NMRI mice weighing 20-25 g 30 min after an intraperitoneal injection of a test compound. Number of mice exhibiting tonic seizures is noted within the next 30 min. At least 3 doses of each test compound are used with 4 or 8 mice per dose, and with doses both above and below the $ED_{50}$ value.

Results.

The $ED_{50}$ value is calculated as the dose in μg/kg where seizures are inhibited in 50% of the animals using a computer program based on the method of Litchfield and Wilcoxon (1949).

THE TABLE

Test results obtained by testing the compound of the invention and the compounds considered to be the closest prior art will appear from the following Table 1.

| | R⁴ | R⁵ | X | in vivo binding ED₅₀ μg/kg | Activity against pentazol induced convulsions ED₅₀ μg/kg | |
|---|---|---|---|---|---|---|
| | | | | | clonic | tonic |
| A (phenyl) | H | CH₃ | N—O / cyclopropyl | 80 | 70 | 30 |
| B (phenyl) | H | CH₃ | N—O / isopropyl | 1,800 | 27,000 | 1,300 |
| C (phenyl) | H | CH₃ | O—N / t-butyl | 600 | 3,000 | 1,700 |
| D (phenyl) | H | CH₃ | O—N / cyclopropyl | 340 | 2,700 | 300 |
| E (Cl-phenyl) | —CH₂CH₂CH₂— | | N—O / cyclopropyl | 960 | 13,000 | 1,000 |

A Compound of the Present invention
B Compound of Ferrosan USP 4,507,313 ex. 3
C Compound of Ferrosan USP 4,507,313 column 2, line 6
D Compound of Roche EP 150,040 ex. 44
E Compound of Roche EP 150,040 ex. 40

From above table it is readily apparent that the compound of the invention is remarkably and unpredictably superior in every respect compared to the most structurally closely-related compounds of the prior art.

In direct comparison to its corresponding 3-cyclopropyl-1,2,4-oxadiazol-5-yl analogue (D) of Roche EP 150,040 (ex. 44) the compound of the invention is more than 4 times as active in binding affinity for the benzodiazepine receptor, approximately 40 times as active in protecting against pentetrazol induced clonic convulsions, and 10 times as active in protecting against pentetrazol induced tonic convulsions.

In direct comparison to the compound E having exactly the same substituted oxadiazol-3-yl substituent, the compound of the invention is 12 times more as active in binding affinity for the benzodiazepine receptor, 185 times as active in protecting against pentetrazol induced clonic convulsions, and 33 times as active in protecting against pentetrazol induced tonic convulsions.

In conclusion, from the foregoing, it is apparent that the present invention provides a novel anticonvulsant and anxiolytic compound 3-(5-cyclopropyl-1,2,4-oxadiazol-3-yl)-5,6-dihydro-5-methyl-6-oxo-4H-imidazo[1,5-a][1,4]benzodiazepine and addition salts thereof, having highly advantageous and unpredictable properties.

Further, a new synthesis is provided by the present invention as well as a new intermediate therefore.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. The compound 3-(5-cyclopropyl-1,2,4-oxadiazol-3-yl)-5,6-dihydro-5-methyl-6-oxo-4H-imidazo[1,5-a][1,4]benzodiazepine having the formula

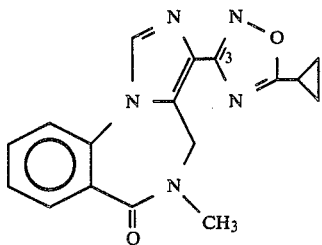

2. A pharmaceutical composition suitable for use in the treatment of a central nervous system ailment comprising an amount of a compound of claim 1 which is effective for the alleviation of such disorder together with a pharmaceutically-acceptable carrier or diluent.

3. A method of treating a central nervous system ailment in a subject in need of such treatment comprising the step of administering to the said subject an amount of a compound of claim 1 which is effective for the alleviation of such ailment.

4. A method of claim 3, wherein the compound is administered in the form of a pharmaceutical composition thereof, in which it is present together with a pharmaceutically-acceptable carrier or diluent.

* * * * *